US012433999B2

(12) United States Patent
Van Der Beek

(10) Patent No.: US 12,433,999 B2
(45) Date of Patent: Oct. 7, 2025

(54) INJECTION DEVICE INCORPORATING A NEEDLE SHIELD REMOVER

(71) Applicant: Novo Nordisk A/S, Bagsvaerd (DK)

(72) Inventor: Willem Van Der Beek, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 599 days.

(21) Appl. No.: 17/801,290

(22) PCT Filed: Feb. 24, 2021

(86) PCT No.: PCT/EP2021/054546
§ 371 (c)(1), (2) Date: Aug. 22, 2022

(87) PCT Pub. No.: WO2021/170647
PCT Pub. Date: Sep. 2, 2021

(65) Prior Publication Data

US 2023/0102922 A1 Mar. 30, 2023

(30) Foreign Application Priority Data

Feb. 25, 2020 (EP) .................................... 20159423

(51) Int. Cl.
*A61M 5/20* (2006.01)
*A61M 5/32* (2006.01)

(52) U.S. Cl.
CPC ............ *A61M 5/20* (2013.01); *A61M 5/3204* (2013.01); *A61M 2005/2006* (2013.01)

(58) Field of Classification Search
CPC .... A61M 5/20; A61M 5/3204; A61M 5/2033; A61M 5/3202; A61M 5/3213; A61M 2005/3109; A61M 2005/2006
See application file for complete search history.

(56) References Cited

U.S. PATENT DOCUMENTS 6,575,939 B1 6/2003 Brunel
7,771,397 B1 8/2010 Olson
(Continued)

FOREIGN PATENT DOCUMENTS

EP 2255842 12/2010
JP 2008500855 A 1/2008
(Continued)

*Primary Examiner* — Tasnim Mehjabin Ahmed
(74) *Attorney, Agent, or Firm* — Wesley Nicolas

(57) ABSTRACT

An injection device (1) comprising a housing (10), a syringe (2) having an injection needle (4) covered by a needle shield (5), and a cap assembly (3) comprising a cap body (15) covering a distal end of the syringe, and a shield remover (9) adapted to engage the needle shield (5), the shield remover (9) being axially fixed relative to the cap body (15). The cap assembly (3) further comprises an elevation member (12) being movable rotationally and axially relative to the cap body (15), wherein the elevation member (12) comprises a first rotation preventing geometry (18, 28, 31) configured to prevent the elevation member (12) from rotating relative to the housing (10), and a cam interface (20) with engaging cam surfaces respectively disposed on the elevation member (12) and the cap body (15), the cam surfaces being configured to engage slidingly upon rotation of the cap body (15) relative to the housing (10) so as to cause a proximal facing surface (17) of the elevation member (12) to be axially forced against a distally facing surface (16) fixedly disposed relative to the housing (10) while moving the cap body (15), the shield remover (9) and the needle shield (5) distally relative to the housing (10).

15 Claims, 6 Drawing Sheets

(56) References Cited

U.S. PATENT DOCUMENTS

| | | | | |
|---|---|---|---|---|
| 2009/0054849 | A1 | 2/2009 | Burnell et al. | |
| 2010/0286619 | A1 | 11/2010 | Abry | |
| 2014/0123479 | A1 * | 5/2014 | Dasbach ............. | A61M 5/3276 29/700 |
| 2018/0311443 | A1 * | 11/2018 | Maxfield ............. | A61M 5/3204 |
| 2018/0353705 | A1 | 12/2018 | Andre et al. | |
| 2020/0330699 | A1 | 10/2020 | Burren et al. | |

FOREIGN PATENT DOCUMENTS

| | | | |
|---|---|---|---|
| JP | 2010540054 | A | 12/2010 |
| JP | 2014520579 | A | 8/2014 |
| WO | 2009019440 | A1 | 2/2009 |
| WO | 2010007395 | A1 | 1/2010 |
| WO | 2013085454 | A1 | 6/2013 |
| WO | 2017029515 | A1 | 2/2017 |
| WO | 2017223354 | A1 | 12/2017 |
| WO | 2018197559 | A1 | 11/2018 |
| WO | 2018202627 | A1 | 11/2018 |
| WO | 2019123073 | A1 | 6/2019 |
| WO | 2019224784 | A1 | 11/2019 |
| WO | 2020074570 | A1 | 4/2020 |

* cited by examiner

INJECTION DEVICE INCORPORATING A NEEDLE SHIELD REMOVER

CROSS-REFERENCE TO RELATED APPLICATIONS

This application is a 35 U.S.C. § 371 National Stage application of International Application PCT/EP2021/054546 (published as WO 2021/170647), filed Feb. 24, 2021, which claims priority to European Patent Application 20159423.1, filed Feb. 25, 2020; the contents of which are incorporated herein by reference.

The present invention relates to injection devices for injecting one or more doses of a liquid drug. In particular the present invention relates to injection devices for injecting one or more doses of drug from a held drug reservoir by means of an injection needle and improvements relating to the safety of the injection device during storage, handling and drug administration.

BACKGROUND

In relation to some diseases patients must inject a medicament on a regular basis such as once weekly, once daily or even a plurality of times each day. In order to help patients overcome fear of needles, some injection devices incorporate a needle shield or needle shroud for covering an injection needle either before or after a dose administration. Such needle shield or shroud typically hide the injection needle from the user's view, and in some forms, additionally provide a mechanical blocking preventing an individual from accidentally gaining access to the injection needle.

Some injection devices incorporate a pre-filled syringe (PFS) wherein the injection needle is typically maintained in a sealed and sterile condition prior to use by a needle shield or "boot". Different types of needle shields have been proposed, some of these include an elastomeric plug that fits over the needle and attaches relative to a neck portion of the barrel of a syringe. The force required for removing the needle shield from the syringe barrel can be quite high, making needle shield removal a cumbersome process, particularly for those with impaired dexterity.

Even in situations where the pre-filled syringe is incorporated in an injection device housing, such as the housing of an auto-injector, and an external cap couples to the needle shield to serve as a tool for handling the needle shield, the removal force can be hard to overcome. Typically, the needle shield is pulled off in an axial direction relative to the syringe barrel. The force can vary due to differences in the dimensions of the parts and the material properties under various circumstances. For alleviating these issues shield-type injection devices have been proposed which have an elevation feature enabling the cap to be twisted off in order to ease the removal of the needle shield. One example is disclosed in EP 2255842 A1. These shield-type injection devices are characterized by visible fairly complex looking technical elevation features on the housing and on the cap enabling the cap to be elevated relatively to the housing while rotating the cap. Such visible elevation features conflict with a potential desire of producing shield-type injection devices with a non-technical, human appearance. A related solution is disclosed in WO 2009/019440 A1 which involves a threaded shield pull component within an outer cap. A further reference WO 2017/029515 A1 provides disclosure of an injection device wherein a mechanism associated with a cap performs a combined priming and needle shield release function.

The known elevation features typically only provide limited axial movement of the needle shield thereby not reaching a satisfying degree of needle shield removal, or requires extensive turning of the cap to enable complete removal. Although the above references include disclosure of cap configurations which is intended to ease the removal process for removing a needle shield from a syringe, there is still a need for injection devices with improved functionality for needle shield removal from a syringe.

SUMMARY

It is an object of the present invention to provide an injection device featuring improved uncapping of a shielded syringe.

The present invention provides for a substantial freedom to design the exterior of a shield-type injection device as any elevation feature is hidden for the user. The invention also includes a freedom to optimize functionality of the hidden elevation features without compromising the esthetical appearance of the device. Furthermore, the invention can be implemented in a number of existing shield-type injection devices with a limited change of design of existing parts and with a limited impact on the assembly process.

In the disclosure of the present invention, embodiments and aspects will be described which will address one or more of the above objects or which will address objects apparent from the below disclosure as well as from the description of exemplary embodiments.

In a first aspect, the present invention relates to an injection device for expelling a drug from a syringe, the injection device comprising:

- a housing formed to be gripped by a subject user, the housing extending along a central longitudinal axis, and defining a distal needle end and an opposite proximal end,
- syringe retaining means,
- a syringe comprising a barrel, the barrel being axially retained relative to the syringe retaining means, an injection needle, and a needle shield arranged over the injection needle; and
- a cap assembly comprising a cap body covering a distal end of the syringe, and a shield remover adapted to engage the needle shield, the shield remover being axially fixed relative to the cap body.

The injection device defines a distally facing surface arranged axially fixed relative to the housing, and a shield removal mechanism comprising a cam interface adapted to axially separate the needle shield from the injection needle upon rotation of the cap body relative to the housing. The cap assembly further comprises an elevation member being movable rotationally and axially relative to the cap body, wherein the elevation member comprises a proximally facing surface configured for engaging the distally facing surface, and wherein the elevation member comprises a first rotation preventing geometry configured to prevent the elevation member from rotating relative to the housing. Said cam interface comprises engaging cam surfaces respectively disposed on the elevation member and the cap body, the cam surfaces being configured to engage slidingly upon rotation of the cap body relative to the housing so as to cause the proximal facing surface of the elevation member to be axially forced against the distally facing surface while moving the cap body, the shield remover and the needle shield distally relative to the housing.

In some embodiments, the injection device further comprises an expelling assembly configured for expelling one or more doses of a drug held by the syringe.

In some embodiments the syringe retaining means is prevented from moving proximally relative to the housing. In other embodiments, the syringe retaining means is prevented from moving proximally and distally relative to the housing. The syringe retaining means may be formed to partly or fully accommodate the syringe barrel of the syringe, and be provided as a syringe holder or a syringe carrier.

In some embodiments the barrel of the syringe is mounted axially fixed relative to the syringe retaining means, e.g. so that the syringe is prevented from moving distally, and optionally, prevented from moving proximally and distally relative to the syringe retaining means.

In other embodiments, the syringe is retained in an axially fixed position relative to the housing in a storage condition, and wherein the syringe is configured for being moved axially relative to the housing from a first position wherein the needle does not protrude from the housing, to a second position wherein the needle protrudes from the housing by a predetermined distance. In such embodiments, the syringe may be configured to move from the first position to the second position in the course of a dose administration, such as upon operation of the expelling assembly.

In further embodiments, the housing, or a component fixedly mounted relative to the housing, forms the distally facing surface.

The injection device may be configured so that it is operable from a storage state to a ready-to-inject state, wherein the cap body and the elevation member assume respective axial storage positions when the injection device assumes the storage state, and wherein the cap body and the elevation member are prevented from moving proximally relative to their respective storage positions.

In some embodiments the injection device comprises a second rotation preventing geometry configured for engagement with the first rotation preventing geometry of the elevation member and configured to prevent the elevation member from rotating relative to the housing when the cap body is rotated relative to the housing, at least during a part of the rotational movement required to axially separate the needle shield from the injection needle.

The injection device may in some embodiments further comprise a needle shroud which is telescopically movable relative to the housing.

The injection device may be formed with a skin contacting member configured to encircle the hollow needle and the needle shield, the skin contacting member being configured for being held against the skin of a user during drug expelling. The skin contacting member may be formed so that it comprises a tubular elongated section arranged coaxially with the injection needle, wherein the tubular elongated section has a distal rim portion. In some forms the skin contacting member forms or defines said needle shroud. In some variants the needle shroud is axially movable for causing the held injection needle to protrude through a central needle aperture in the needle shroud. In other forms the skin contacting member forms a distal most face of the housing of the injection device. In such variants, the syringe barrel is axially slideable relative to the housing causing the held injection needle to protrude through the central needle aperture of the skin contacting member.

In embodiments including a needle shroud, the needle shroud may cooperate with the housing so that the needle shroud is prevented from moving rotationally relative to the housing, and wherein the needle shroud comprises said second rotation preventing geometry.

In alternative embodiments, the housing, or a component fixedly attached to the housing, comprises said second rotation preventing geometry.

The first rotation preventing geometry of the elevation member may comprise one or more axially extending ledges, each being rotationally locked relative to a respective axially extending ledge of the second rotation preventing geometry.

In some variants, the second rotation preventing geometry is formed on a radially outwards facing surface cooperating with the first rotation preventing geometry arranged on a radially inwards facing surface of the elevation member. In other variants, the second rotation preventing geometry is formed on a radially inwards facing surface cooperating with the first rotation preventing geometry arranged on a radially outwards facing surface of the elevation member. In still other variants, the second rotation preventing geometry is formed on a distally facing surface cooperating with the first rotation preventing geometry arranged on a proximally facing surface of the elevation member. Such variant may comprise a distally facing flange comprising said second rotation preventing geometry provided by at least one depression or protrusion arranged at said distally facing flange, and wherein the first rotation preventing geometry of the elevation member engages the at least one depression or protrusion at said distally facing flange to provide a rotational lock between the elevation member and housing.

In some variants the elevation member is formed as a sleeve shaped member arranged coaxially between the shield remover and the cap body. In embodiments that include a needle shroud, the sleeve shaped member may in some embodiments be arranged coaxially between the needle shroud and the cap body.

In certain embodiments, the elevation member is fully comprised within the cap body when the injection device assumes the storage state. In some embodiments, when the cap body has been rotated fully relative to the elevation member, the elevation member is still fully comprised within the cap body. In other embodiments, upon rotation of the cap body relative to the elevation member, the elevation member may be brought to protrude from the cap body.

In still further embodiments, a distal portion of the elevation member is comprised within the cap body, and wherein a proximal portion of the elevation member extends proximally from the cap body, even when the injection device assumes the storage state.

To provide a rotational stop limitation, geometries of the cap body and the elevation member, such as the cam interface, may comprises a pair of cooperating rotational end blockers defining an end-of-rotation blocking position between the cap body and the housing.

To provide a rotational start limiting position, geometries of the cap body and the elevation member, such as the cam interface, may be comprise a pair of cooperating rotational start blockers defining a start-of-rotation blocking position between the cap body and the housing.

To aid in instructing the user in proper use of the injection device, the device may be formed to comprise a first indicator signifying rotation of the cap body relative to the housing. Optionally, a second indicator may be provided signifying axially pulling of the cap body relative to the housing. In such embodiments, the injection device may be so configured as to reveal, in response to rotation of the cap body, said second indicator.

The cap assembly may in still further embodiments comprise a ratchet mechanism, such as a click mechanism, provided between the cap body and the elevation member, wherein the ratchet mechanism is configured to provide tactile feedback clicks in the course of the distal movement of the cap body relative to the elevation member during rotation of the cap body relative to the housing. Such ratchet mechanism may either be configured as a one-way ratchet mechanism or as a two-way ratchet mechanism.

When the proximally facing surface of the elevation member axially engages the distally facing surface, the distally facing surface prevents the elevation member from moving proximally. In this way it is ensured that the cap body performs a helical movement relative to the housing as the cap body is rotated relative to the housing.

In some forms of the cap assembly, the shield remover is mounted freely rotatable relative to the cap body. In other embodiments, the shield remover is either fixedly mounted relative to the cap body, or formed as a single unitary component with the cap body.

As used herein, the term "drug" is meant to encompass any drug-containing flowable medicine or combinations of separately held plurality of drug-containing flowable medicines capable of being passed through a delivery means such as a cannula or hollow needle in a controlled manner, such as a liquid, solution, gel or fine suspension.

BRIEF DESCRIPTION OF DRAWINGS

In the following the invention will be further described with reference to the drawings, wherein.

Figure 1:
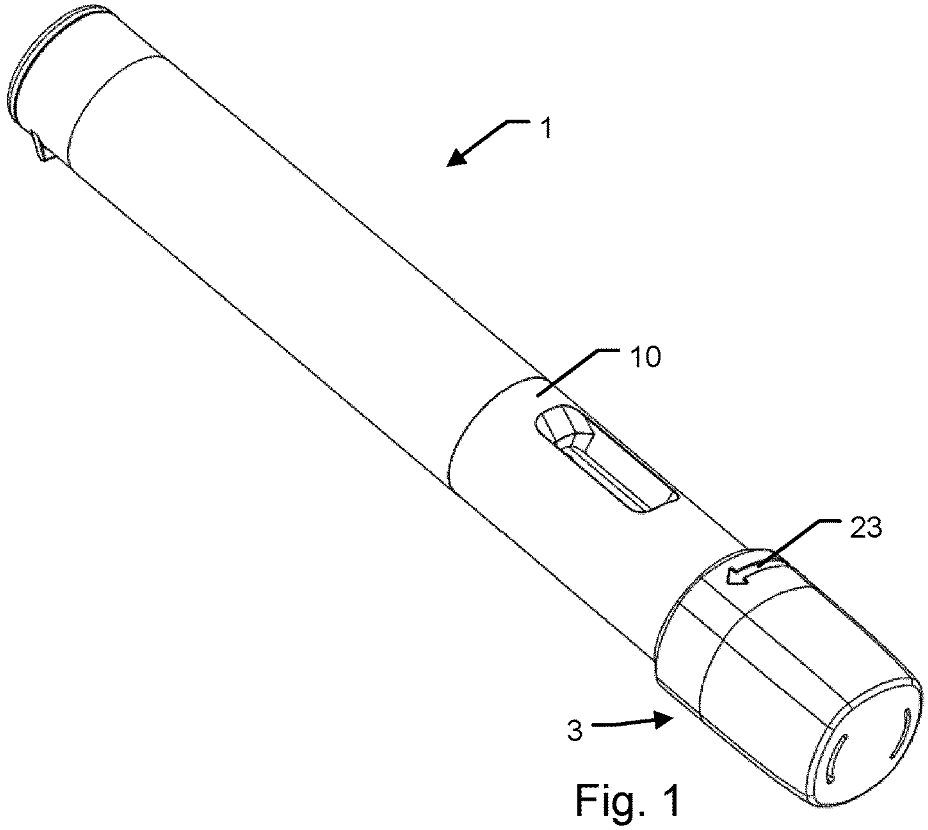
FIG. 1 shows a perspective view of a first embodiment of an injection device 1 in accordance with the present invention, during storage of the device before initial use.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DESCRIPTION

In the context of the present disclosure it may be convenient to define that the term "distal end" in the appended figures is meant to refer to the end of the injection device which usually carries the injection needle whereas the term "proximal end" is meant to refer to the opposite end of the injection device pointing away from the injection needle. The shown figures are schematical representations for which reason the configuration of the different structures as well as the relative dimensions are intended to serve illustrative purposes only.

FIG. 1 shows a first embodiment of a shield-type injection device 1 accommodating a prefilled syringe 2 that comprises a needle 4 and a protective needle shield 5. The injection device 1 is shown in a storage state. The device comprises an elongated housing 10 extending along a central longitudinal axis and having a proximal end and a distal end. A cap assembly 3 is attached to the distal end of the housing 10.

Figure 2:
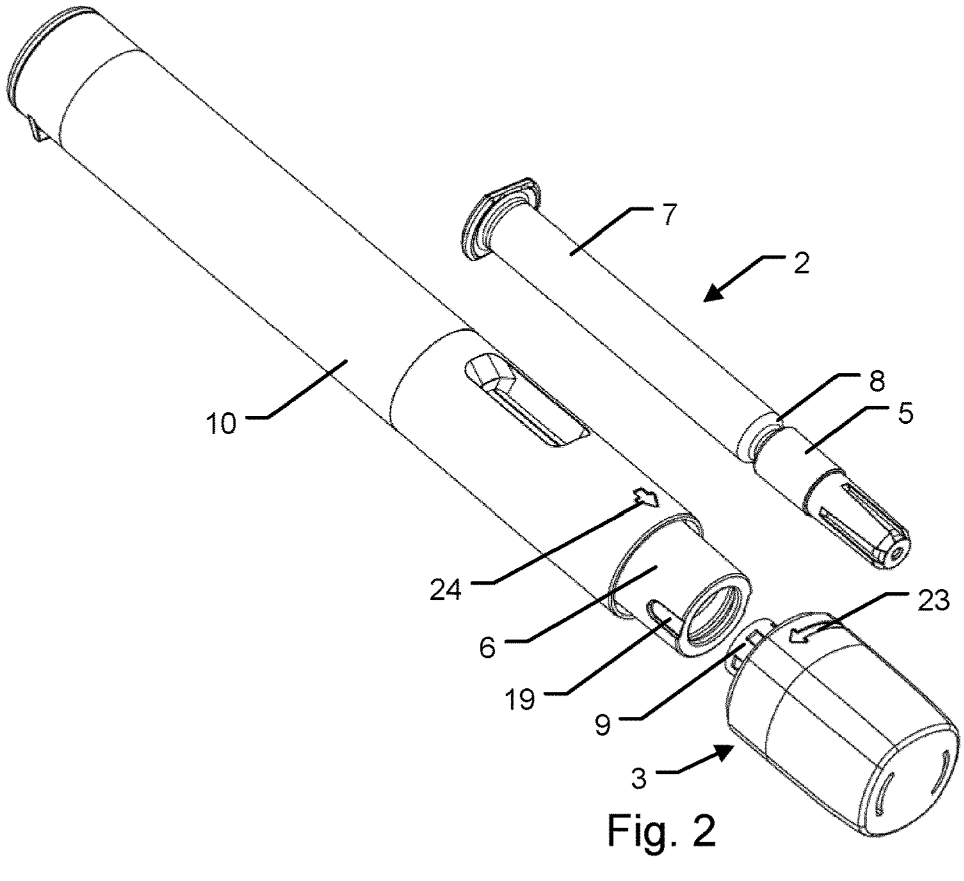
FIG. 2 shows a partly exploded perspective view of the injection device 1 of FIG. 1 with a cap assembly 3 and syringe 2 separated from a housing 10.
Figure 3:
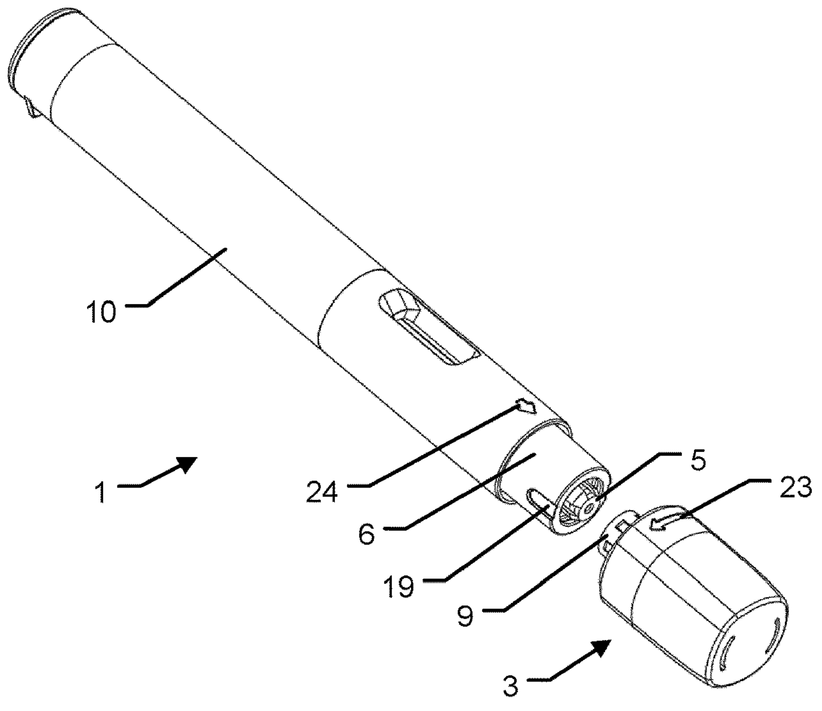
FIG. 3 is a perspective view of the injection device 1 of FIGS. 1-2 with the cap assembly 3 separated from the housing 10.

FIG. 2 shows the injection device 1 in a view wherein the syringe 2 and the cap assembly 3 are shown separated from the housing 10. In different levels of assembly, FIGS. 3 and 4 provide further views of the sub-assemblies and components of the injection device 1.

Figure 4:
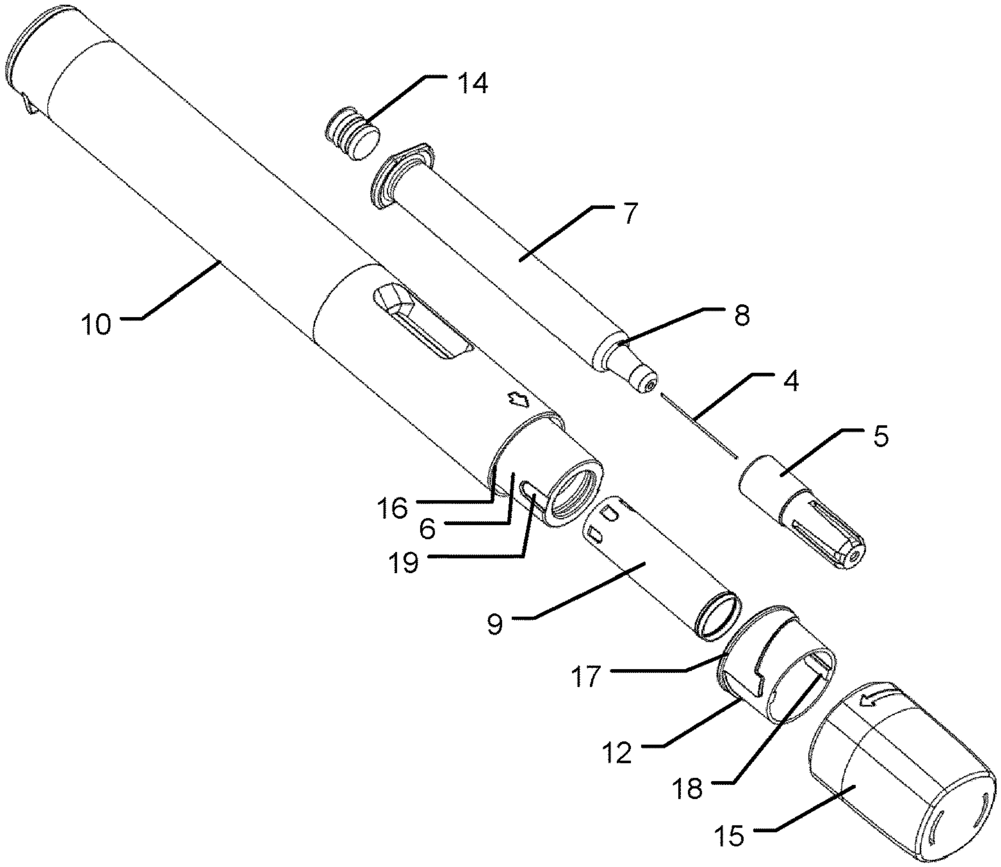
FIG. 4 is a view corresponding to FIG. 2 but wherein the cap assembly 3 and the syringe are shown exploded.

FIGS. 2 and 4 show a standard prefilled syringe (PFS) as widely used in industry. The syringe 2 comprises a tubular barrel 7 having a neck portion 8 located distally wherein the neck portion has a reduced diameter compared to the diameter of the barrel 7. An injection needle 7 is mounted to the neck portion 8 and a removable cap provided in the form of a rigid needle shield (RNS) 5 is attached to the neck 8 so that the needle shield 5 sealingly and sterilely seals off the needle 4. Internally in the barrel 7 a slideably arranged piston 14 is arranged. A drug may be accommodated within the barrel between the piston 14 and the needle 4. Although the shown syringe only incorporates a single piston 14, other configurations may incorporate multiple pistons for accommodation and expelling of one or more drugs, including drugs to be reconstituted before administration. The syringe 2 depicted in FIG. 2 further includes a proximally arranged finger flange extending radially from the wall of the barrel. For the shown syringe, a circumferential gap exists between the barrel 7 of the syringe and the needle shield 5 covering the needle 4.

In the shown embodiment, a syringe retaining feature 11 (only showed in FIG. 6*a*-6*c*) in the injection device 1 is configured to fixedly retain the syringe 2 when accommodated in the housing 10. An expelling mechanism, such as a spring-drive expelling mechanism (not shown) accommodated within housing 10 will is configured to push a piston of a mounted syringe distally while the syringe retaining feature 11 prevents the syringe barrel from moving distally. For simplicity, the expelling mechanism will not be discussed further, but may be configured as either a manual expelling mechanism or an automated expelling mechanism, such as a spring-driven or electrically driven expelling mechanism. Also, the syringe retaining feature will not be further discussed within this disclosure but may be configured as part of the housing 10 or as a separate syringe holder mounted relative to the housing. Different exemplary syringe holder principles may be employed, such as the ones disclosed in WO 2019/081578A1 and WO 2013/089620 A1. The housing 10, or a separate syringe holder, may retain the syringe 2 against distal movement by cooperating with a reduced diameter neck part arranged at a distal end of the syringe barrel and/or by cooperating with a flange arranged at proximal end of the syringe barrel. In further embodiments the syringe retaining feature may be provided as part of a syringe carrier that retains the syringe against distal movement relative the syringe carrier, where the syringe carrier is mounted axially movable relative to the housing, such as disclosed in WO 2009/019440 A1.

In the shown embodiment, a needle shroud 6 covers the needle 4 prior to injection and after injection. In the storage state of the injection device, and after dose administration, the cap assembly 3 covers the needle 4 and the needle shroud 6. As mentioned above, in the shown embodiment, the needle 4 is covered by a protective needle shield 5, such as a Rigid Needle Shield (RNS), that fits tight around the neck portion 8 of the syringe barrel 7 of the prefilled syringe 2 to protect bacteria's to pass between the syringe barrel 7 and the protective needle shield 5 in the area were the protective needle shield and the syringe barrel 7 part of the prefilled syringe 2 are connected.

The cap assembly 3 comprises a cap body 15 shaped to be gripped by the fingers of a user and sized to fit over the needle shield 5 and the needle shroud 6. Cap assembly 3 further features a shield remover 9 gripping the protective needle shield 5 in a manner that, upon user-initiated dose administration, the protective needle shield 5 is removed from the syringe barrel 7 by removal of the cap assembly 3 from the injection device 1, thus leaving the needle 4 uncovered. To enable the cap body 15 to be rotated the shield remover 9 is mounted freely rotatable within the cap body 15 but in a manner wherein axial movement between cap body 15 and shield remover 9 is prohibited. Hence, as the shield remover is coupled to the needle shield 5 axial movement of the cap body 15 relative to housing 10 will result in axial movement of the needle shield 5 relative to the barrel 7 of syringe 2.

Figure 10:
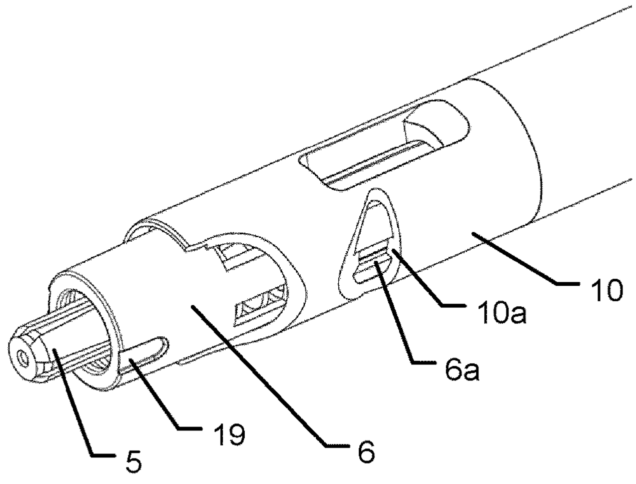
FIG. 10 shows a partly cut perspective view of the front portion of the injection device shown in FIGS. 1-9*b,*
Figure 11:
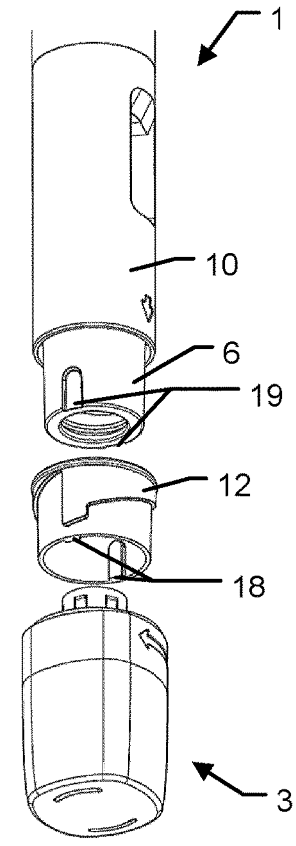
FIG. 11 shows a further perspective exploded view of components of the cap assembly 3 and the front portion of the injection device 1 shown in FIGS. 1-10, FIGS. 12*a* and 12*b* show two perspective exploded view of components of a cap assembly 3 and a front portion of a second embodiment of an injection device in accordance with the present invention.

Although not mandatory in connection with the broadest aspect of the present invention, the shown exemplary injection device 1 includes a needle shroud 6 protecting the needle 4 in a manner to generally obscure the needle from view. The needle shroud 6 is mounted telescopically in the housing 10 so that in the initial storage state a distal portion of the needle shroud 6 extends from the housing 10. Referring to FIG. 10, the needle shroud 6 and the housing 10 include spline features 6*a*, 10*a* so that the needle shroud 6 is axially movable relative to the housing but prevented from rotating. The needle shroud 6 is axially movable relative to housing 10 from an extended position wherein the needle 4 is both covered and concealed into a collapsed position wherein the needle 4 is exposed so that the needle extends a predefined distance from a distal end face of the needle shroud. In the shown embodiment, the needle shroud 6 is reversibly movable relative to the housing so that the needle shroud is movable from the extended position into the collapsed position and further back to the extended position.

In use, the needle shroud 6 is pushed against the body to enable, e.g. triggering, an injection. A needle shroud spring 13 enables the needle shroud 6 to be forced back to the extended position where the needle 4 again is covered once the pressure from pushing the needle shroud 6 against the body is relieved.

In addition to the cap body 15 and the shield remover 9, the cap assembly 3 comprises an elevation member 12, enabling the cap assembly 3 to be twisted off the protective needle sheath 5 to be pulled off the needle 4 when twisting off the cap body 15 relative to the housing 10. The shield remover 9 is illustrated as a separate part permanently attached to the cap body 15 in a manner enabling the shield remover 9 to remain in a stationary rotational position relative to the needle shroud 6, the syringe barrel 7 and the housing 10 once the cap body is twisted off whereas the cap body 15 is changing its rotational and axial position. The shield remover 9 remains in the same axial position as the cap body 15 once the cap body is twisted off. Thus, the shield remover 9 is a separate part of the cap assembly 3 attached to the cap body 15 to only enable a rotational movement. The purpose of a rotationally attached shield remover 9 is to enable the protective needle sheath 5 to be removed from the needle 4 and the syringe barrel neck 8 in an axial direction once the cap body 15 is twisted. In the shown embodiment, the elevation member 12 is formed as a sleeve shaped member arranged coaxially between the shield remover 9 and the cap body 15, i.e. in a manner wherein the elevation member is fully accommodated within the cap body 15. In the shown embodiment, although not identifiable in the figures, the elevation member 12 is mounted axially slideable within the cap body between axial end limits. Referring to FIG. 4, the proximal rim of the elevation member 12 forms a proximally facing surface 17 configured to engage a distally facing surface 16 provided as a distal facing rim portion of the housing 10.

A cam interface 20 is arranged between the cap body 15 and elevation member 12. The cam interface in the shown embodiment is formed as elevation tracks provided as helical cam surfaces disposed on the cap body 15 and the elevation member 12, respectively. The cam interface 20 enables the cap body 15 to be elevated in the distal direction in the course of the cap body 15 being turned by the user. As the elevation member 12 is locked rotationally to the needle shroud 6 by ridges 18 on the inside of the elevation member 12 fitting into recesses 19 in the outer surface of the needle shroud 6 the helical cam surfaces are forced to slidingly engage each other as the cap body 15 is twisted relative to the housing 10 and, as a consequence, the elevation member 12 is forced proximally relative to the cap body 15. As the proximally facing surface 17 on elevation member 12 is pressed towards the distal facing rim portion of the housing 10 the cap body 15 is forced axially in the distal direction relative to housing 10 and syringe 7. As a result the shield remover 9 and the needle shield 5 is detached axially from the neck portion 8 of the barrel of the syringe 2.

The ridges 18 and the recesses 19 are formed in a manner enabling the cap assembly 3 including the elevation member 12 to be interconnected in an axial direction to the needle shroud 6 during assembly and to also being entirely removed from the rest of the injection device 1 by pulling the cap assembly 3 including the elevation member 12 in an axial direction after the cap body 15 has been rotated sufficiently, or at any time the user would like to pull off the cap assembly 3 instead of twisting off the cap assembly 3. In the shown first embodiment, a precondition for the elevation member 12 to be rotationally locked when twisting the cap body 15 relative to the housing is the fact that the needle shroud 6 is rotationally locked to the housing 10.

Figure 5A:
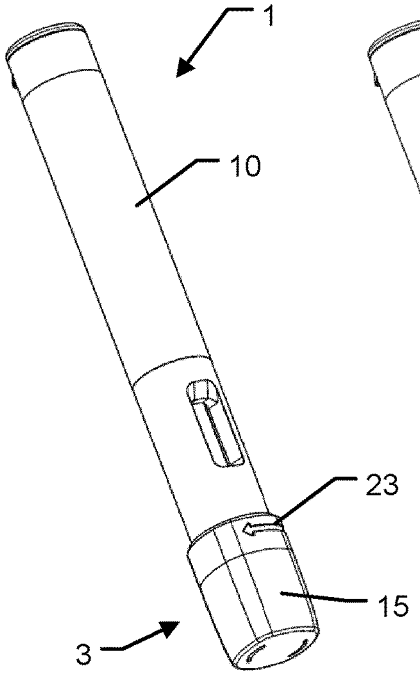
FIGS. 5*a*, 5*b* and 5*c* show perspective views of the first embodiment injection device 1 in three states during cap removal.
Figure 5B:
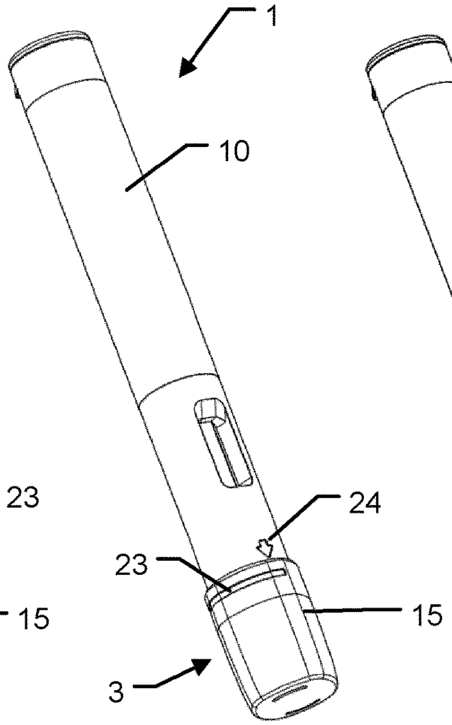
Figure 5C:
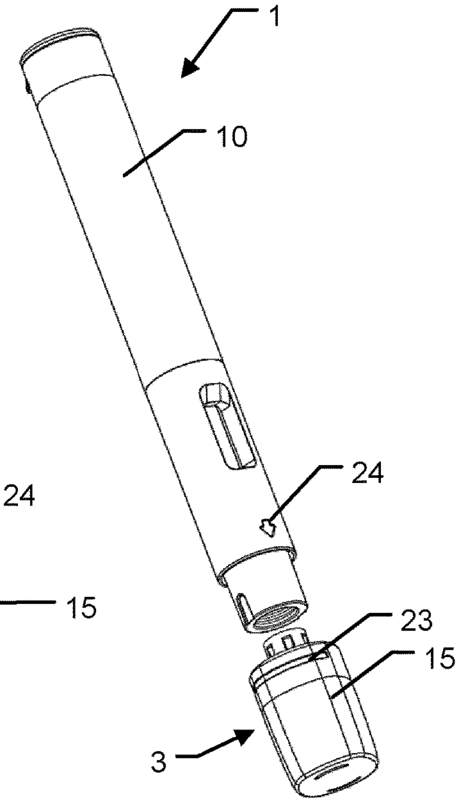
Figure 6A:
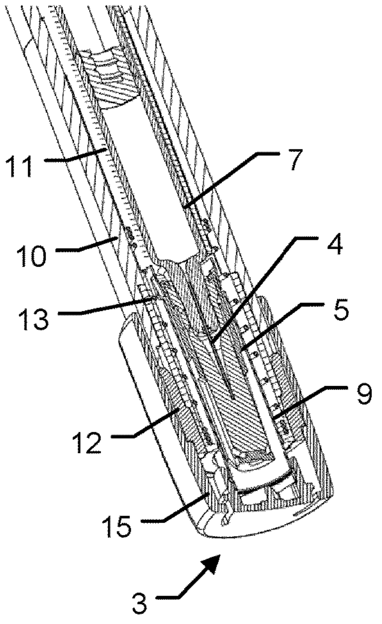
FIGS. 6*a*, 6*b* and 6*c* are perspective cross-sectional views corresponding to FIGS. 5*a*, 5*b* and 5*c,*
Figure 6B:
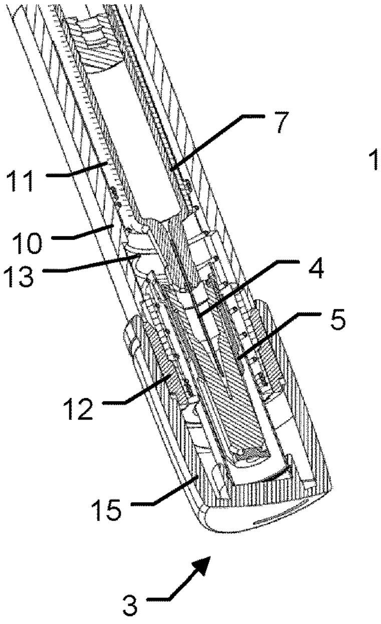
Figure 6C:
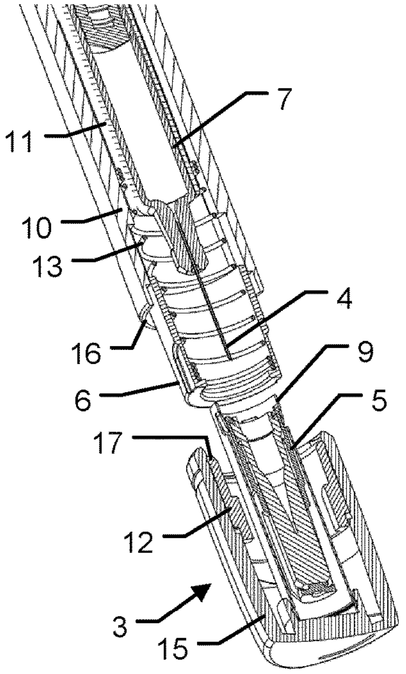

Reference is now made to FIGS. 5*a* to 5*c* which show the injection device and cap assembly in three consecutive states during cap removal. Accompanying cross-sectional views are shown in FIGS. 6*a*-6*c*. When holding the housing 10 of the injection device in one hand and the cap assembly 3 between the fingers of the other hand during removal of the cap assembly 3 the cap assembly removal is intended to be carried out by twisting the cap body 15 relative to the housing. For the shown embodiment, the elevation member 12 is rotationally locked relative to the needle shroud 6, and furthermore rotationally locked relative to the housing 10. A common way to rotationally lock a needle shroud 6 to a housing 10 is a track and a slot or vice versa in respectively the needle shroud 6 and the inner surface of the housing 10 as shown in FIG. 10. To distribute forces evenly when twisting the cap assembly 3, the cap body 15 and the elevation member 12 are forced away from each other by two sets of elevation tracks 20 positioned rotationally 180 degrees apart, i.e. in a symmetrical manner. The elevation tracks 20 in the cap body 15 and the elevation member 12 are formed with an elevation geometry optimized to overcome the forces required to move the protective needle sheath 5 from the needle 4 and the syringe barrel neck 8. The cap assembly 3 is twisted in one direction and thus the two sets of elevation tracks 20 can be as long as necessary taking simple tooling to manufacture the parts into consideration and taking into consideration that the best possible gearing to overcome forces to remove the protective needle sheath 5 requires a good balance between the length of the elevation tracks 20 and the elevation grade.

Figure 9A:
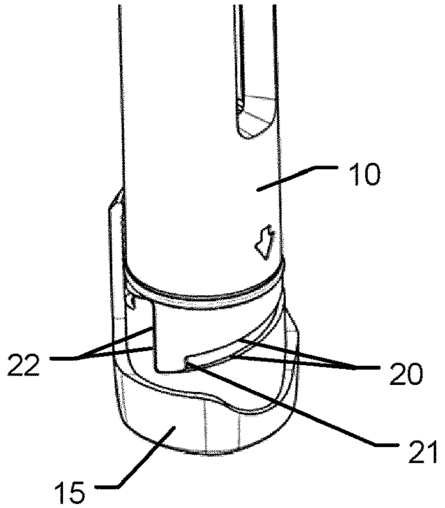
FIG. 9*a* shows a partly cut perspective view of the components of FIG. 8 in an assembled state, wherein the components are shown in the storage state.
Figure 9B:
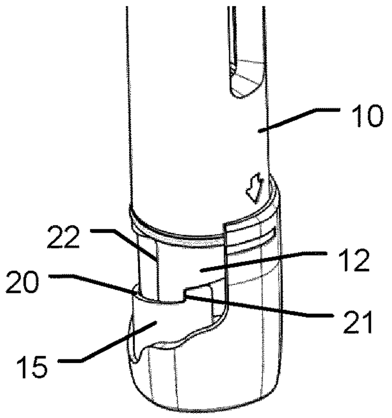
FIG. 9*b* is a view corresponding to FIG. 9*a* but wherein the component are shown in a state during cap removal.

To provide tactile feedback for the user that the cap assembly 3 is rotated sufficiently and that it is time for the cap assembly 3 to be removed by simply pulling the cap assembly 3 away from the housing 10, the cam interface may include rotational end blockers, which in the shown embodiment are formed as cooperating axially extending ledges 21 (See FIG. 9*b*). To enable the cap assembly 3 to be only twisted in one direction at the start of the twisting action the cam interface 20 will additionally be provided with rotational start blockers, which in the shown embodiment are formed as cooperating axially extending ledges 22 (see FIG. 9*a*).

Figure 7:
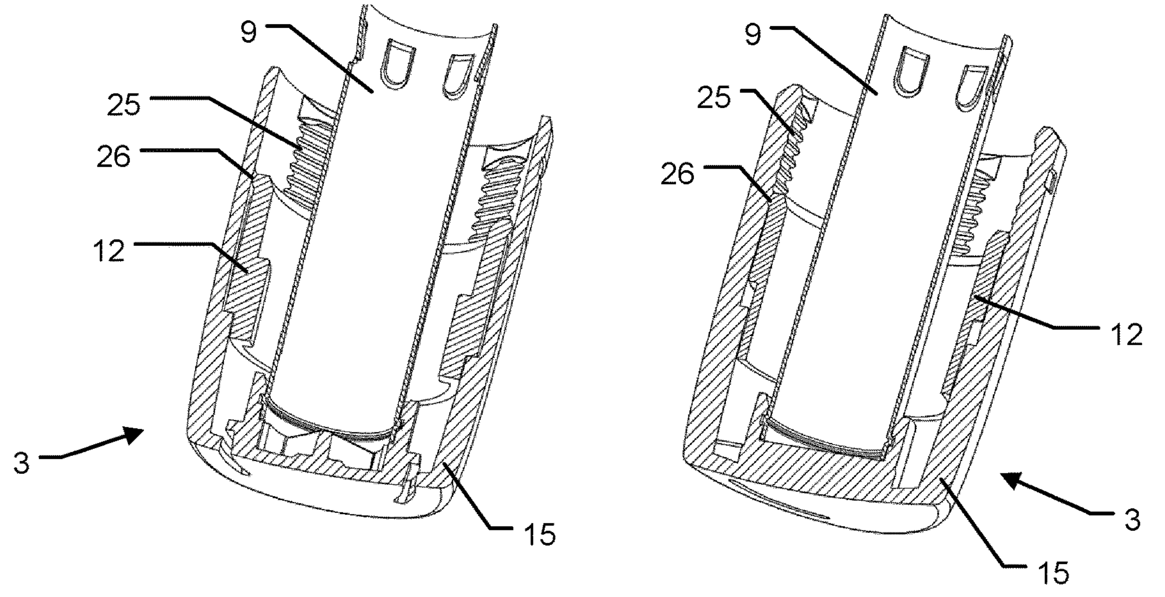
FIG. 7 shows two different detailed perspective cross-sectional views of the cap assembly of the first embodiment of the injection device 1.
Figure 8:
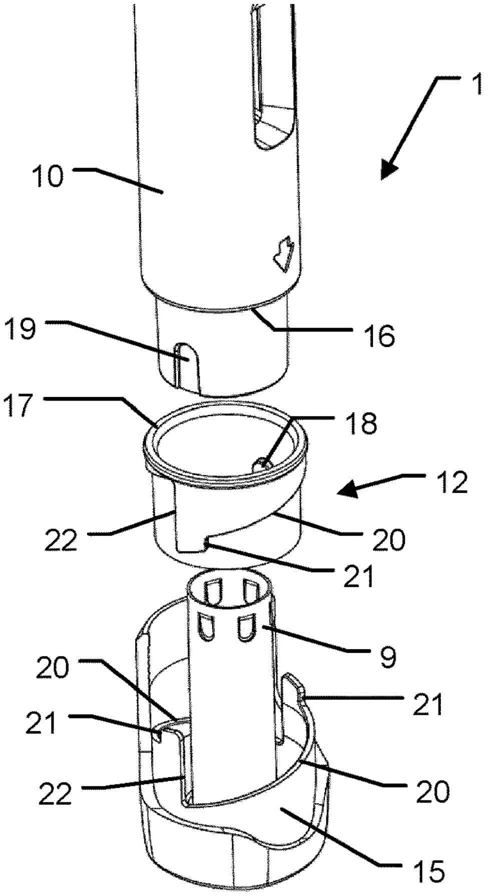
FIG. 8 shows a partly cut perspective exploded view of components of the cap assembly 3 and the front portion of the injection device 1 shown in FIGS. 1-7.

Furthermore, the cap assembly 3 and the housing 10 may show a visual indication feature to guide the user to the steps to be made to remove the cap assembly 3. A rotation arrow 23 on the front of the cap body 15, or both on the front and on the rear side of the cap body 15, tells the user how to rotate the cap assembly 3. As shown in the first embodiment, a pull arrow 24 may be arranged on a radial outer surface of housing 10. Once the cap body 15 is rotated to its end position, accompanied by axial movement of the cap body, the pull arrow 24 on the housing 10, which initially has been hidden by the cap body 15, has appeared and is aligned with the end of the longer horizontal line portion of the rotation arrow 23. This is an indication for the user that it is time to fully remove the cap assembly 3 by pulling the cap assembly 3 away from the rest of the injection device 1. To enable the elevation member 12 to always be positioned in a well-defined manner under the cap assembly 3 there are formed support ribs 25 on the inside of the cap body 15 and a corresponding elevation member upper rim 26 to hold the elevation member 12 in position. Once the cap assembly 3 is rotated the support ribs 25 give a tactile feedback to the user and function as an invisible indication that two elements are moving relative to each other as the elevation member upper rim 26 will slide over the support ribs 25 (cf. FIG. 7).

Figure 12A:
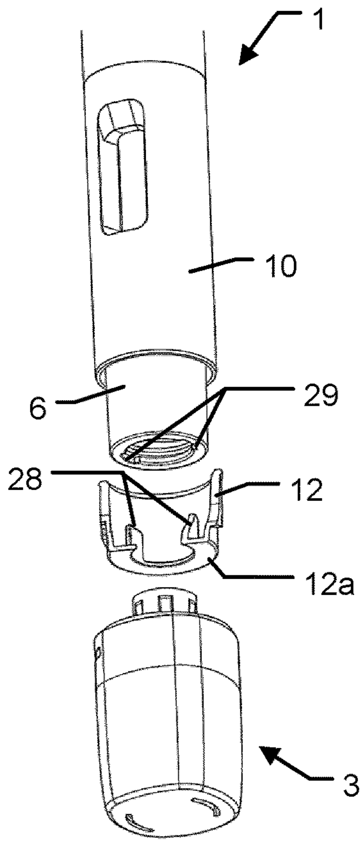
Figure 12B:
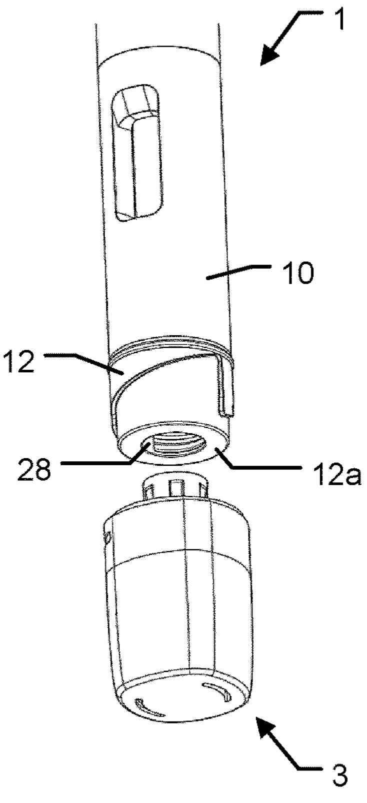

As described above, the cap assembly 3 is provided with an elevation member 12 which is rotationally locked relative to the needle shroud 6 by means of a physical engagement between the elevation member 12 and the needle shroud 6 providing the rotational lock between the two parts but also enabling an axial disengagement of the elevation member 12 from the needle shroud 6. In the first embodiment the elevation member 12 is locked rotationally to the needle shroud 6 by ridges 18 on the radial inwards surface of the elevation member 12 fitting into recesses 19 in the radial outwards facing surface of the needle shroud 6. There are two ridges 18 and two recesses 19 as described in order to obtain sound kinematics for the construction versus e.g. one ridge 18 and one recess 19. However, the geometries may in alternative embodiments be provided, by making e.g. three or more sets of ridges 18 and recesses 19. A substitute for ridges 18 and recesses 19 could be a regular triangular-, square-, pentagon-, or hexagon shapes, or other equilateral shapes or any other variation of shapes enabling the above-mentioned rotational lock and the axial disengagement. Also, the choice of ridges 18 on the inner of the elevation member 12 fitting into recesses 19 in the outer surface of the needle shroud 6 could be made differently as ridges 18 could be disposed on the outer surface of the needle shroud 6. Instead of making a suitable geometry on the outside of the needle shroud 6, any geometry enabling the rotational lock and the axial disengagement could be situated on a radially inwards surface of the needle shroud 6. FIGS. 12*a* and 12*b* shows a second embodiment of an injection device 1 where the geometry of the inner edge 27 of the distal facing surface 12*a* is formed with two recesses 29 cooperating with two raised flanges 28 on the inside of the elevation member 12, where the two raised flanges 28 points in the proximal direction.

The shield remover 9 in the drawings is illustrated as a separate part permanently attached to the cap body 15 in a manner enabling the shield remover 9 to remain in a stationary rotational position relative to the needle shroud 6, the syringe barrel 7 and the housing 10 once the cap assembly 3 is twisted off whereas the cap body 15 is changing both its rotational and axial position relative to the housing 10. The shield remover 9 remains in the same axial position as the cap body 15 once the cap assembly 3 is twisted off. Thus, the shield remover 9 is a separate part, attached to the cap body 15 in a way that enables the shield remover to rotate freely relative to the cap body 15. The purpose of a rotation function related to the shield remover 9 is to enable the protective needle sheath 5 to be removed from the needle 4 and the neck 8 of the syringe barrel 7 in an axial direction once the cap assembly 3 is twisted. This type of shield remover 9 is well known in the art. Other embodiments of the injection device 1 may be formed with a cap assembly 3 were the shield remover 9 is a non-separate part integrated in the cap body 15, formed in a way that it will hook on the protective needle sheath 5 during assembly and will pull off the protective needle sheath 5 from the neck 8 of the syringe barrel 7 and the needle 4 once the cap assembly 3 is rotated or simply pulled off. In such embodiment it is possible to rotate the cap body 15, including the integrated shield remover 9 relative to the protective needle sheath 5 during removal of the cap assembly 3 and accordingly the protective needle sheath 5 following the axial movement of the cap. Thus, also in this case, the protective needle sheath 5 will be removed in an axial direction.

Whatever the shield remover 9 is an integrated part of the cap body 15, or it is a separate part, attached to the cap body 15, the elevation member 12 can be integrated in either concept. The figures show two sets of elevation tracks 20 positioned rotationally 180 degrees from each other and the elevation tracks 20 end with end stop walls 21 parallel to the central longitudinal axis of the injection device 1. To enable the cap assembly 3 to be only twisted in one direction when starting the twisting of the cap assembly 3 the start stop walls 22 provide such rotational blocking. It can be chosen to leave out the end stop walls 21, resulting in a less preferable user feedback. It is also possible to only form either the elevation tracks 20 only in the cap body 15 or only in the elevation member 12. In that case ridges in either the cap body 15 or the elevation member 12 could follow the elevation tracks and 20 once the cap assembly 3 is rotated in order to push the cap assembly 3 off the injection device 1. Instead of two elevation tracks 20, or two sets of elevation tracks 20, it is possible to provide alternative embodiments with three elevation tracks 20, or three sets of elevation tracks 20. It is also possible to form the tracks as mirrored tracks, forming V-shapes. In that case the cap assembly 3 can be removed by rotation in either direction, clock-wise or anti-clock-wise.

Figure 13:
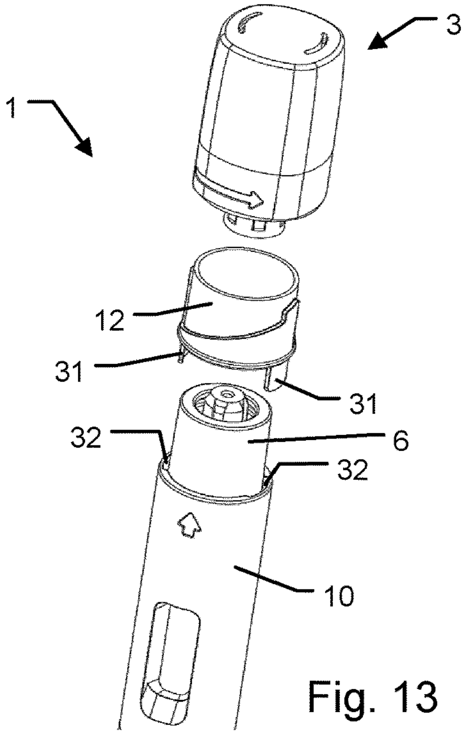
FIG. 13 is a perspective exploded view of components of a cap assembly 3 and a front portion of a third embodiment of an injection device in accordance with the present invention.

Instead of linking the elevation member 12 to the needle shroud 6 for enabling the rotational lock and relative axial displacement, the elevation member 12 may be linked directly to the housing 10. FIG. 13 shows a third embodiment of an injection device 1, wherein flanges 31 extend proximally from a proximal end rim of the elevation member 12. The flanges 31 cooperate with recesses 32 on an interior surface of the housing 10 to provide the rotational lock and enable the elevation member to be pulled axially relative to the housing 10.

Figure 14A:
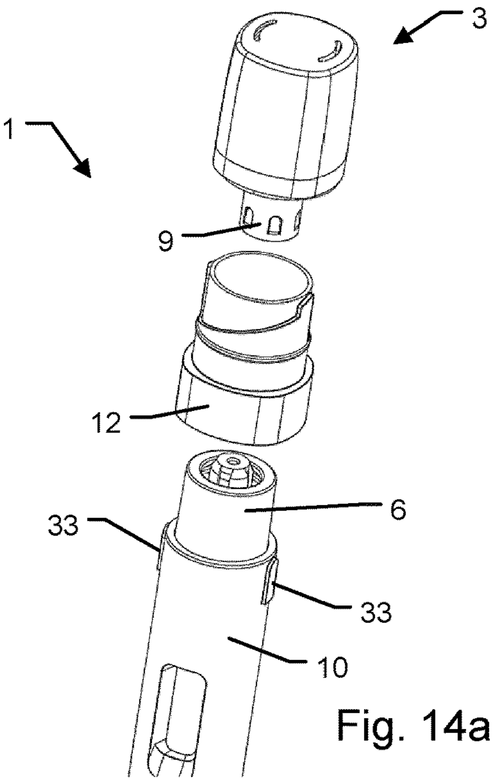
FIG. 14*a* is a perspective exploded view of components of a cap assembly 3 and a front portion of a fourth embodiment of an injection device in accordance with the present invention.
Figure 14B:
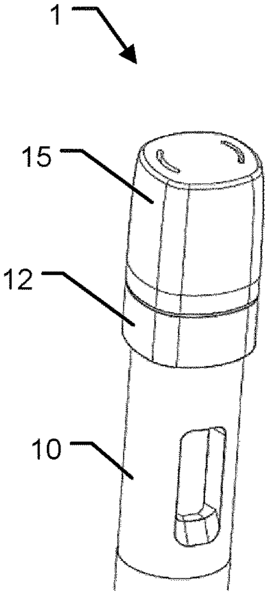
FIGS. 14*b*, 14*c* and 14*d* show perspective views of the fourth embodiment injection device shown FIG. 14*a*, the device being shown in three states during cap removal.
Figure 14C:
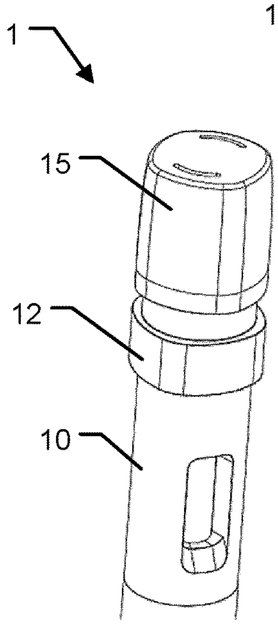
Figure 14D:
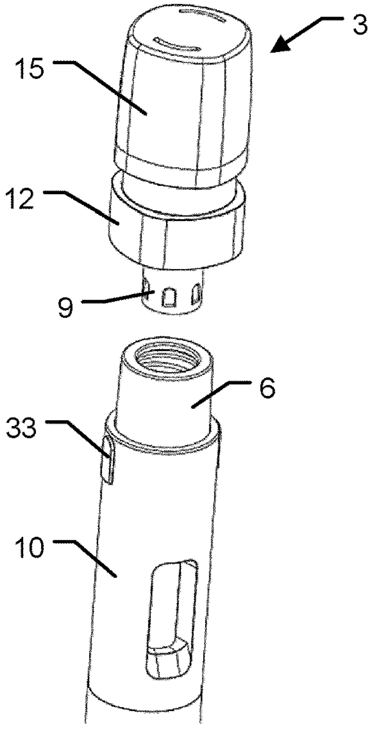

FIG. 14*a* shows a fourth embodiment of an injection device 1 where the elevation member 12 has a section that fits over the distal end portion of the housing 10. This section of the elevation member 12 will extend proximally from the cap body 15, and thus be visible. The cap assembly 3 therefore appear as a two-piece cap. FIG. 14*b*, which shows the device in its storage state prior to removal of the cap assembly 3, reveals that there is a natural transition from the cap body 15 to the elevation member 12. After initial rotation (FIG. 14*c*) wherein the needle shield 5 is at least partly axially separated from the neck portion 8 of syringe 2, the cap body 15 will have axially separated from the elevation member 12 by predetermined distance. Typically, depending on the particular embodiment, this axial distance will be sufficient for the needle shield to fully disengage the neck portion 8 of the syringe. However, in other embodiments, the predefined distance only correspond to a major part of the axial movement required for fully disengaging from the neck portion. Upon subsequent axially pulling of the cap body 15 relative to the housing 10, the elevation member 12 will follow axial movement of the cap body, and the cap body 15, the elevation member 12, the shield remover 9 and the needle shield 5 will be removed from the remaining of the device as a single entity (FIG. 14*d*).

The rotational lock is secured by a geometry ensuring rotational locking of the elevation member 12 relative to the housing 10, while enabling axial movement therebetween. In FIGS. 14*a*-14*d* the ridges 33 on the radially outwards facing surface of the housing 10 cooperate with recesses (not shown) disposed on the interior side of the elevation member 12. An elevation member fitting over the main housing as illustrated in FIGS. 14*a*-14*d* may alternatively have flanges that fit to recesses on the inside of the housing 10, instead of cooperating with the exterior geometry 33 of the housing.

The description above with respect to the figures has been provided to give background information on the use of an exemplary injection device applicable for use with the present invention. However, the injection device described is one of many different available injection devices that can be utilized with the principles according to the present invention. It should be stressed that the invention is not limited to the shown embodiment and the described variants but may be embodied in other ways within the subject matter defined in the following claims and within the remaining disclosure.

The invention claimed is:

1. An injection device for expelling a drug from a syringe, the injection device comprising:

a housing formed to be gripped by a subject user, the housing extending along a central longitudinal axis, and defining a distal needle end and an opposite proximal end, syringe retaining means, a syringe comprising a barrel mounted relative to the syringe retaining means, an injection needle, and a needle shield arranged over the injection needle; and a cap assembly comprising a cap body covering a distal end of the syringe, and a shield remover adapted to engage the needle shield, the shield remover being axially fixed relative to the cap body;

wherein the injection device defines:

a distally facing surface arranged axially fixed relative to the housing, and a shield removal mechanism comprising a cam interface adapted to axially separate the needle shield from the injection needle upon rotation of the cap body relative to the housing, wherein the cap assembly further comprises an elevation member being movable rotationally and axially relative to the cap body, wherein the elevation member comprises a proximally facing surface configured for engaging the distally facing surface, and wherein the elevation member comprises a first rotation preventing geometry configured to prevent the elevation member from rotating relative to the housing, wherein said cam interface comprises engaging cam surfaces respectively disposed on the elevation member and the cap body, the cam surfaces being configured to engage slidingly upon rotation of the cap body relative to the housing so as to cause the proximal facing surface of the elevation member to be axially forced against the distally facing surface while moving the cap body, the shield remover and the needle shield distally relative to the housing.

2. The injection device as in claim 1, wherein the injection device comprises a second rotation preventing geometry configured for engagement with the first rotation preventing geometry of the elevation member and configured to prevent the elevation member from rotating relative to the housing when the cap body is rotated relative to the housing.

3. The injection device as in claim 2, further comprising a needle shroud which is telescopically movable relative to the housing but prevented from moving rotationally relative to the housing, and wherein the needle shroud comprises said second rotation preventing geometry.

4. The injection device as in claim 2, wherein the housing, or a component fixedly attached to the housing, comprises said second rotation preventing geometry.

5. The injection device as in claim 1, wherein the first rotation preventing geometry of the elevation member comprises one or more axially extending ledges, each being rotationally locked relative to a respective axially extending ledge of the second rotation preventing geometry.

6. The injection device as in claim 1, wherein either:

the second rotation preventing geometry is formed on a radially outwards facing surface cooperating with the first rotation preventing geometry arranged on a radially inwards facing surface of the elevation member, or the second rotation preventing geometry is formed on a radially inwards facing surface cooperating with the first rotation preventing geometry arranged on a radially outwards facing surface of the elevation member.

7. The injection device as in claim 1, wherein the injection device comprises a distally facing flange comprising said second rotation preventing geometry provided by at least one depression or protrusion arranged at said distally facing flange, and wherein the first rotation preventing geometry of the elevation member engages the at least one depression or protrusion at said distally facing flange to provide a rotational lock between the elevation member and housing.

8. The injection device as in claim 1, wherein the elevation member is fully comprised within the cap body.

9. The injection device as in claim 1, wherein a distal portion of the elevation member is comprised within the cap body, and wherein a proximal portion of the elevation member extends proximally from the cap body.

10. The injection device as in claim 1, wherein the cam interface comprises a pair of cooperating rotational end blockers defining an end-of-rotation blocking position between the cap body and the housing.

11. The injection device as in claim 1, wherein the cam interface includes a pair of cooperating rotational start blockers defining a start-of-rotation blocking position between the cap body and the housing.

12. The injection device as in claim 1, wherein the injection device comprises a first indicator signifying rotation of the cap body relative to the housing and a second indicator signifying axially pulling of the cap body relative to the housing, wherein the injection device is configured to reveal, in response to rotation of the cap body, said second indicator.

13. The injection device as in claim 1, wherein the cap assembly further comprises a ratchet mechanism provided between the cap body and the elevation member, and wherein the ratchet mechanism is configured to provide tactile feedback on the distal movement of the cap body relative to the elevation member during rotation of the cap body relative to the housing.

14. The injection device as in claim 1, wherein, when the proximally facing surface of the elevation member axially engages the distally facing surface, the distally facing surface prevents the elevation member from moving proximally.

15. The injection device as in claim 1, wherein the shield remover is mounted freely rotatable relative to the cap body.

* * * * *